US007327872B2

(12) United States Patent
Vaillant et al.

(10) Patent No.: US 7,327,872 B2
(45) Date of Patent: Feb. 5, 2008

(54) METHOD AND SYSTEM FOR REGISTERING 3D MODELS OF ANATOMICAL REGIONS WITH PROJECTION IMAGES OF THE SAME

(75) Inventors: Régis Vaillant, Villabon sur Yvette (FR); Jasbir Singh Sra, Pewaukee, WI (US); Jean Cousty, Neuilly sur Seine (FR); François Kotian, Guyancourt (FR)

(73) Assignees: General Electric Company, Schenectady, NY (US); Jasbir S. Sra, Pewaukee, WI (US)

( * ) Notice: Subject to any disclaimer, the term of this patent is extended or adjusted under 35 U.S.C. 154(b) by 639 days.

(21) Appl. No.: 10/964,429

(22) Filed: Oct. 13, 2004

(65) Prior Publication Data

US 2006/0078195 A1     Apr. 13, 2006

(51) Int. Cl.
*G06K 9/00* (2006.01)
*G06K 9/32* (2006.01)
*A61B 6/00* (2006.01)
*G06F 19/00* (2006.01)

(52) U.S. Cl. .................. 382/154; 382/128; 382/294
(58) Field of Classification Search ............ 382/128, 382/130, 131, 132, 154, 285, 293, 294, 295, 382/296; 600/424, 427, 425; 345/419, 619, 345/630, 634, 653, 664, 679
See application file for complete search history.

(56) References Cited

U.S. PATENT DOCUMENTS 3,954,098 A    5/1976  Dick et al. ............... 128/2.05 Z

| 4,574,807 A | 3/1986 | Hewson et al. ....... 128/419 PG |
| 5,245,287 A | 9/1993 | Nowak et al. ............... 324/322 |
| 5,274,551 A | 12/1993 | Corby, Jr. ............... 364/413.13 |
| 5,304,212 A | 4/1994 | Czeisler et al. ............... 607/88 |
| 5,348,020 A | 9/1994 | Huston ....................... 128/696 |

(Continued)

FOREIGN PATENT DOCUMENTS

EP     1182619 A2     8/2001

(Continued)

OTHER PUBLICATIONS

J. Sra et al., "Electroanatomically Guided Catheter Ablation of Ventricular Tachycardias Causing Multiple Defibrillator Shocks;" PACE 2001; vol. 24; 1645-52.

(Continued)

*Primary Examiner*—Yon J. Couso
(74) *Attorney, Agent, or Firm*—Cantor Colburn LLP

(57) ABSTRACT

An imaging system for use in a medical intervention procedure is disclosed. A first image acquisition system of a first modality employing a catheter at an anatomical region of a patient is configured to produce a first image of the anatomical region using fluoroscopy, the first image comprising a set of fluoroscopy projection images. A second image acquisition system of a second different modality is configured to generate a 3D model of the anatomical region. An anatomical reference system is common to both the first and second image acquisition systems. A processing circuit is configured to process executable instructions for registering the 3D model with the fluoroscopy image in response to the common reference system and discernible parameters associated with the catheter in both the first and second image acquisition systems.

29 Claims, 5 Drawing Sheets

U.S. PATENT DOCUMENTS

| | | | |
|---|---|---|---|
| 5,353,795 A | 10/1994 | Souza et al. | 128/653.2 |
| 5,391,199 A | 2/1995 | Ben-Haim | 607/122 |
| 5,431,688 A | 7/1995 | Freeman | 607/10 |
| 5,515,849 A | 5/1996 | Murashita et al. | |
| 5,568,384 A | 10/1996 | Robb et al. | 364/419.13 |
| 5,738,096 A | 4/1998 | Ben-Haim | 128/653.1 |
| 5,752,522 A | 5/1998 | Murphy | 600/587 |
| 5,823,958 A | 10/1998 | Truppe | 600/426 |
| 5,839,440 A | 11/1998 | Liou et al. | 600/431 |
| 5,951,475 A | 9/1999 | Gueziec et al. | 600/425 |
| 6,058,218 A | 5/2000 | Cline | |
| 6,081,577 A | 6/2000 | Webber | 378/23 |
| 6,154,516 A | 11/2000 | Heuscher et al. | 378/19 |
| 6,208,347 B1 | 3/2001 | Migdal | 345/419 |
| 6,233,304 B1 | 5/2001 | Hu et al. | 378/8 |
| 6,235,038 B1 | 5/2001 | Hunter et al. | 606/130 |
| 6,246,898 B1 | 6/2001 | Vesely et al. | 600/424 |
| 6,249,693 B1 | 6/2001 | Cline et al. | 600/410 |
| 6,252,924 B1 | 6/2001 | Davantes et al. | 378/8 |
| 6,256,368 B1 | 7/2001 | Hsieh et al. | 378/8 |
| 6,266,553 B1 | 7/2001 | Fluhrer et al. | 600/428 |
| 6,289,115 B1 | 9/2001 | Takeo | 382/130 |
| 6,289,239 B1 | 9/2001 | Panescu et al. | 600/523 |
| 6,298,259 B1 | 10/2001 | Kucharczyk et al. | 600/411 |
| 6,314,310 B1 | 11/2001 | Ben-Haim et al. | 600/424 |
| 6,325,797 B1 | 12/2001 | Stewart et al. | 606/41 |
| 6,348,793 B1 | 2/2002 | Balloni et al. | 324/309 |
| 6,353,445 B1 | 3/2002 | Babula et al. | 345/733 |
| 6,381,485 B1 | 4/2002 | Hunter et al. | 600/407 |
| 6,389,104 B1 | 5/2002 | Bani-Hashemi et al. | 378/98.12 |
| 6,411,848 B2 | 6/2002 | Kramer et al. | 607/9 |
| 6,421,412 B1 | 7/2002 | Hsieh et al. | 378/9 |
| 6,456,867 B2 | 9/2002 | Reisfeld | 600/407 |
| 6,468,265 B1 | 10/2002 | Evans | 606/1 |
| 6,490,475 B1 | 12/2002 | Seeley et al. | 600/426 |
| 6,490,479 B2 | 12/2002 | Bock | 600/518 |
| 6,504,894 B2 | 1/2003 | Pan | 378/8 |
| 6,549,606 B1 | 4/2003 | Vaillant et al. | 378/4 |
| 6,556,695 B1 | 4/2003 | Packer et al. | 382/128 |
| 6,584,343 B1 | 6/2003 | Ransbury et al. | 600/509 |
| 6,650,927 B1 | 11/2003 | Keidar | 600/424 |
| 6,782,284 B1 | 8/2004 | Subramanyan et al. | 600/407 |
| 6,991,605 B2 * | 1/2006 | Lim | 600/443 |
| 2002/0010392 A1 | 1/2002 | Desai | 600/374 |
| 2002/0046756 A1 | 4/2002 | Laizzo et al. | 128/899 |
| 2002/0138108 A1 | 9/2002 | Kralik | 607/9 |
| 2003/0018251 A1 | 1/2003 | Solomon | 600/427 |
| 2003/0023266 A1 | 1/2003 | Borillo et al. | 606/200 |
| 2003/0028183 A1 | 2/2003 | Sanchez et al. | 606/34 |
| 2003/0065260 A1 | 4/2003 | Cheng et al. | 600/427 |
| 2003/0097219 A1 | 5/2003 | O'Donnell et al. | 702/19 |
| 2003/0120264 A1 | 6/2003 | Lattouf | |
| 2003/0187358 A1 | 10/2003 | Okerlund et al. | 600/443 |
| 2003/0220557 A1 | 11/2003 | Cleary | 600/409 |
| 2004/0027347 A1 | 2/2004 | Farsaie | 345/419 |
| 2004/0087850 A1 | 5/2004 | Okerlund et al. | 600/407 |
| 2004/0225212 A1 | 11/2004 | Okerlund et al. | 600/407 |
| 2004/0225328 A1 | 11/2004 | Okerlund et al. | 607/9 |
| 2004/0225331 A1 | 11/2004 | Okerlund et al. | 607/14 |

FOREIGN PATENT DOCUMENTS

| | | |
|---|---|---|
| EP | 1321101 A2 | 12/2002 |
| WO | WO 91/07726 | 5/1991 |
| WO | WO96/10949 | 10/1994 |
| WO | WO 96/10949 | 4/1996 |
| WO | WO91/07726 | 11/2001 |

OTHER PUBLICATIONS

J. Sra et al., "Feasibility and Validation of Registration of Three-Dimensional Left Atrial Models Derived From Computed Tomography With a Noncontact Cardiac Mapping System;" Heart Rhythm Society 2005; vol. 2; No. 1: 55-63.

Sra et al., "Registration of Three-Dimensional Left Atrial Computed Tomographic Images With Projection Images Obtained Using Fluoroscopy", Circulation 2005; 112: 3763-3768.

Genevieve Derumeaux et al., Doppler Tissue Imaging Quantitates Regional Wall Motion During Myocardial Ischemia and Reperfusion, Circulation Journal of the American Heart Association, Circulation 1998; 97; 1970-1977.

Olivier Gerard et al., Efficient Model-Based Quantification of Left Ventricular Function in 3-D Echocardiography. IEEE Transactions on Medical Imaging, 21 (9): pp. 1059-1068, Sep. 2002.

Wahle et al., 3D Heart Vessel Reconstruction from Biplane Angiograms, IEEE Computer Graphics and Applications, 16(1): pp. 65-73, Jan. 1996.

Helmut Mair et al., Epicardial Lead Implantation Techniques for Biventricular Pacing via Left Lateral Mini-Thoracotomy, Video Assisted Thoracoscopy and Robotic Approach, The Heart Surgery Forum, 6(5): pp. 412-417, Mar. 2003.

Toshiko Nakai, Michael D. Lesh, Edward P. Gerstenfeld, Renu Virmani, Russell Jones and Randall J. Lee; "Percutaneous Left Atrial Appendage Occlusion (PLAATO) for Preventing Cardioembolism: First Experience in Canine Model", Circulation 2002; 105;2217-2222; originally published online Apr. 15, 2002; American Heart Association; http://circ.ahajounals.org/cgi/content/full/105/18/2217.

Jasbir Sra, David Krum, Angela Malloy, Melissa Vass, Barry Belanger, Elisabeth Soubelet, Regis Vaillant and Masood Akhtar. "Registration of Three-Dimensional Left Atrial Computed Tomographic Images With Projection Images Obtained Using Fluoroscopy." Journal of the American Heart Association. Circulation 2005;112;3763-3768. Copyright 2005 American Heart Association. http://circ.ahajournals.org/cgi/content/full/112/24/3763.

F. E. Marchlinski et al., "Linear Ablation Lesions for Control of Unmappable Ventricular Tachycardia in Patients With Ischemic and Nonischemic Cardiomyopathy;" Circulation 2000; 1288-96.

Biosense Webster a Johnson&Johnson company, "CARTO Cardiac Electrophysiological Mapping System Training Manual;" Apr. 2000.

H. Nikagawa et al., "Role of the Tricuspid Annulus and the Eustachian Valve/Ridge on Atrial Flutter: Relevance to Catheter Ablation of the Septal Isthmus and a New Technique for Rapid Identification of Ablation Success;" Circulation 1996; 94:407-24.

L. Gepstein et al., "A Novel Method for Nonfluoroscopic Catheter-Based Electroanatomical Mapping of the Heart: In Vitro and In Vivo Accuracy Results;" Circulation 1997; 95:1611-22.

S. Shpun et al., "Guidance of Radiofrequency Endocardial Ablation with Real-time Three-dimensional Magnetic Navigation System;" Circulation 1997; 96:2016-21.

J. Sra et al., "Electroanatomic Mapping to Identify Breakthrough Sites in Recurrent Typical Human Flutter;" Paceing Clin. Electrophysiol 2000; 23:1479-92.

R.J. Schilling et al.; "Simultaneous Endocardial Mapping in the Human Left Ventricle Using a Noncontact Catheter: Comparison of Contact and Reconstructed Electrograms During Sinus Rhythm;" Circulation 1998; 98:997-98.

C. C. Gornick et al., "Validation of a New Noncontact Catheter System for Electroanatomic Mapping of Left Ventricular Endocardium;" Circulation 1999; 99:829-835.

J. Sra et al., "Noncontact Mapping for Radiofrequency Ablation of Complex Cardiac Arrhythmias;" J. Interven. Cardiac Electrophysiol 2001; 5:323-331.

N. M.S. de Groot et al., "Three-Dimensional Catheter Positioning During Radiofrequency Ablation in Patients: First Application of a Real-Time Position Management System;" J. Interven. Cardiac Electrophysiol 2001; Nov. 11(11):1183-92.

J. Schreieck et al., "Radiofrequency Ablation of Cardiac Arrhythmias Using a Three-Dimensional Real-Time Position Management and Mapping System;" Pacing Clin. Ekectrophysiol, Dec. 25, 2002(12):1699-707.

F. Wittkampf et al., "Real-Time, Three-Dimensional, Nonfluoroscopic Localization of the Lasso Catheter;" J. Interven. Cardiac ElectrophysiolI 2002, 13:630.

J. Sra et al., "Cardiac Chamber Geometry Construction, Catheter Navication and Ablation Using Cutaneous Patches;" *Supplement to Circulation* Oct. 2003, 108 (17): IV-585, Abstract 2667.

J. Sra et al., "Three-Dimensional Right Atrial Geometry Construction and Catheter Tracking Using Cutaneous Patches;" *J. Interven. Cardiac Electrophysiol*, 2003 14:897.

Z. Zhang; "Iterative Point Matching for Registration of Free-Form Curves;" *Inria* 1992, pp. 1-40.

C.L. Grines et al.; "Functional Abnormalities in Isolated Left Bundle Branch Block: The Effect of Interventricular Asynchrony;" *Circulation*: 1989; 79:845-53.

H. B. Xia et al., "Differing effects of right ventricular pacing and left bundle branch block on left ventricular function;" *Br. Heart J.*, 1993; 69:166-173.

S. Cazeau et al., "Effects of Multisite Biventricular Pacing in Patients with Heart Failure and Intraventricular Conduction Delay;" *N. Engl. J. Med.* 2001; 344:873-880.

M. V. Pitzalis et al., "Cardiac Resynchronization Therapy Tailored by Echocardiographic Evaluation of Ventricular Acnchrony;" *J. Am. Coll. Cardiol.* 2002; 40:1615-22.

W. T. Abraham et al., "Cardiac Resynchronization in Chronic Heart Failure;" *N. Engl. J. Med.* 2002; 346:1845-1853.

C. A. Pelizzari et al., "Accurate Three-Dimensional Registration of CT, PET, and/or MR Images of the Brain;" *J. Comput. Assist. Tomogr.* 1989; 13:20-26.

A.C. Evans et al.; "MRI-PET Correlation in Three Dimensions Using a Volume-of-Interest (VOI) Atlas;" *J. Cerb Flow Metab.* 1991; 11:A69-A78.

R.P. Woods et al.; "Rapid Automated Algorithm for Aligning and Reslicing PET Images;" *Journal of Computer Assisted Tomography*, 1992; 16:620-633.

B.A. Ardekani et al.; "A Fully Automatic Multimodality Image Registration Algorithm;" *Journal of Computer Assisted Tomography*; 1995; 19:615-623.

L. Thurfell et al.; "Registration of Neuroimaging Data: Implementation and Clinical Applications;" *American Society of Neuroimaging*; 2000; 10:39-46.

S. A. Ben-Haim et al.; "Nonfluoroscopic, in vivo navigation and mapping technology;" *Nature Medicine*; 1996, 2:1393-5.

B. Taccardi et al.; "A new intracaitary probe for detecting the site of origin of ectopic ventricular beats during one cardiac cycle;" *Circulation*; 1987; 75:272-81.

F. H.M. Wittkampf et al.; "New Technique for Real-Time 3-Dimensional Localization of Regular Intracardiac Electrodes;" *Circulation*; 1999; 99:1312-17.

V. Fuster et al. "ACC/AHA/NASPE 2002 Guidelines Update for Implantation of Pacemakers and Antiarrhythmia Devices;" *J. Am Coll. Cardiol* 2001; 38:1-47.

D. R. Ney "Volumetric Rendering of Computed Tomography Data: Principles and Techniques;" *IEEE Computer Graphics and Applications*; 1990; 24-32.

N. M. Alpert et al., "The Principal Axes Transformation—A Method for Image Registration;" *The Journal of Nuclear Medicine*; 1990; 31:1717-1722.

P.A. van den Elsen et al.; "Medical Image Matching—A Review with Classification;" *IEEE Engineering in Medicine and Biology*, 1993; 26-38.

G. T. Barnes et al.; "Conventional and Spiral Computed Tomography: Physical Principles and Image Quaility Considerations;" *Computed Body Tomography*, 1998, Lippincot-Raven, Philadelphia, PA pp. 1-20.

Milan Sonka and J. Michael Fitzpatrick (eds); *Handbook of Medical Imaging vol. 2 Medical Image Processing and Analysis*; pp. 129-174 & 447-506, Jun. 2000.

W. M. Feinberg et al.; "Prevalence, Age Distribution, and Gender of Patients with Atrial Fibrillation;" *Arch. Intern. Med.* vol. 155; Mar. 1995; pp. 469-473.

J. L. Cox, J. P. Boineau, R. B. Schuessler, T. B. Ferguson, Jr., M. E. Cain, B. D. Lindsay, P. B. Corr, K. M. Kater, D. G. Lappas; "Operations for Atrial Fibrillation;" Electrophysiology, Pacing and Arrhythmia, Clin. Cardiol. 14, 1991; pp. 827-834.

M. Haissaguerre, P. Jais, S. C. Shah, A. Takahashi, M. Hocini, G. Quiniou, S. Garrigue, A. Le Mouroux, P. Le Metayer, and J. Clementy; "Spontaneous Initiation of Atrial Fibrilliation by Ectopic Beats Originating in the Pulmonary Viens;" The New England Journal of Medicine, vol. 339, No. 10, Sep. 3, 1998; pp. 659-668.

C. Pappone, S. Rosanio, G. Augello, G. Gallus, G. Vicedomini, P. Mazzone, S. Gulletta, F. Gugliotta, A. Pappone, V. Santinelli, V. Tortoriello, S. Sala, A. Zangrillo, G. Crescenzi, S. Benussi, and O. Alfieri; "Mortality, Morbidity, and Quality of Life After Circumferential Pulmonary Vein Ablation for Atrial Fibrillation;" Journal of the American College of Cardiology, vol. 42, No. 2; 2003; 185-197.

J. Sra et al., "Current Problems in Cardiology- Atrial Fibrilliation: Epidemiology, Mechanisms, and Management;" Current Problems in Cardiology, Jul. 2000; pp. 406-524.

ACC/AHA/ESC Practise Guidelines; Eur. Heart J., vol. 22, Oct. 2001; pp. 1854-1923.

M. D. Leash, T. Trepelse, H. Omran, A. Bartorelli, P. Della Bella, T. Nakai, M. Reisman, D. fleschenberb, U. Krumsdorf, and D. Scherer; "Tiny Device Blocks 'Usless' Part of Heart, prevents blood clots;" Journal Report; American Heart Association; Apr. 9, 2002.

Ellen Barlow; "Operating in 3-D" found at www.med.harvard.edu/publications/HMAB/196fo3d.html, Jul. 2002.

PCT Search Report for PCT/US2004/020909.

"Advanced Vessel Analysis" product descritpoin, [online] http://www.gehealthcare.com/usen/ct/clin_app/products/aswessel.html [retrieved Dec. 1, 2004].

"CardilQ" product description, [online], http://egems.gehealtcare.com/geCommunity/Europe/flex_trial/awFlexTrial/aw3_l/eflextrial [retrieved Dec. 1, 2004].

* cited by examiner

METHOD AND SYSTEM FOR REGISTERING 3D MODELS OF ANATOMICAL REGIONS WITH PROJECTION IMAGES OF THE SAME

BACKGROUND

This invention relates generally to a medical imaging system, and more particularly to a method and apparatus for registering 3D models of anatomical regions with projection images of the same.

During a number of interventional procedures related to the improvement of electrical therapy in the heart, the physician has to manipulate catheters and/or leads inside the heart chambers. An example of the two most complex and common procedures include atrial fibrillation (AF) ablation, and bi-ventricular pacing.

Atrial fibrillation, an arrhythmia in which the atria (upper chambers of the heart) stop contracting as they fibrillate, is the most common of the heart rhythm problems. In United States alone it is estimated that there are over 2 million people who have atrial fibrillation. Present data suggest that it is the most common arrhythmia-related cause of hospital admissions. Patients with AF tend to have a high incidence of such complications as stroke and congestive heart failure. Premature atrial contractions may act as triggers and initiate paroxysms of AF. These premature atrial contractions have been shown to predominantly originate in the pulmonary veins from the left atrium. Since infrequent and non reproducible premature atrial contractions may limit the utility of ablating trigger sites, a variety of surgical and catheter techniques have been used to isolate the pulmonary veins from the left atrium.

One of the surgical techniques used to treat (ablate) AF involves applications of radiofrequency waves to create small scars on the heart's surface near the connection between the pulmonary veins and the left atrium. The small scars created by the radiofrequency waves tend to stop the erratic impulses of atrial fibrillation by directing the impulses to follow a normal electrical pathway through the heart. Typically, this type of surgical procedure is performed through a chest incision. Surgeons use specially designed instruments to deliver radiofrequency waves to the abnormal tissue, typically during the open heart surgery performed for other reasons, such as valve surgery or bypass surgery for example. Although this type of surgical technique is effective when the patient is undergoing open heart surgery for another reason, catheter-related treatment methods are more practical when the patient does not require the invasive open heart surgery for other reasons.

One of the catheter techniques involves fluoroscopic guided positioning of catheter in the left atrium after going through a blood vessel, and the application of radiofrequency energy at areas showing double potentials suggestive of sites capable of conducting between the left atrium and the pulmonary veins. It has also been shown that ablation at other sites such as between the mitral valve and left pulmonary veins, and between the pulmonary veins, as is done during the surgical intervention, may increase the success rate of AF ablation. The three-dimensional reconstruction of the left atrium using some currently available technologies, the inability of the physician to visualize the pulmonary vein ostia (opening of these veins into the left atrium) from inside, the varying size of the pulmonary veins and thus the pulmonary vein ostia, the difficulty in keeping the mapping and ablation catheters stable at the pulmonary vein ostial site due to the complex 3D geometry of these areas, all make current approaches to mapping and ablation using current fluoroscopically guided techniques somewhat cumbersome and lengthy. Because of these limitations, surgery has been preferred over radiofrequency catheter ablation, especially in patients with persistent atrial fibrillation, and it is estimated that less than 20 percent of patients with persistent AF undergoing radiofrequency ablation for AF, benefit from this approach.

A factor that may be associated with the above mentioned limitation is that the operator typically guides an interventional tool using mainly the fluoroscopy images. A typical task in such a procedure is the placement of a catheter at a specific location, such as one of the pulmonary veins for example. These anatomical structures are not well depicted by the x-ray system since they do not present contrast versus the surrounding anatomical structures.

The medical task would be much easier if these target anatomical structures were visible in the fluoroscopy image in the precise anatomic fashion separate from the surrounding anatomic structures.

Another important procedure, as mentioned above, involves bi-ventricular pacing in the treatment of heart failure. Despite considerable progress in the management of congestive heart failure (CHF), it remains a major health problem worldwide. It is estimated that there are 6-7 million people with CHF in the United States and Europe, and approximately 1 million patients are diagnosed with CHF every year.

Despite significant advances in the treatment of CHF using various pharmacological therapies, quality-of-life in patients with CHF is poor as they are frequently hospitalized, and heart failure is a common cause of death. In addition, there is significant cost attached to this problem.

Normal electrical activation in the heart involves activation of the upper chambers, called the atria, followed by simultaneous activation of both the right and the left lower chambers, called the ventricles, by the left and right bundle branches. As patients with advanced CHF may have conduction system disease, which may play a role in worsening cardiac function, pacing therapies have been introduced in an attempt to improve cardiac function. One frequently noted conduction abnormality is left bundle branch block (LBBB). In one study, (Xiao HB, et al. Differing effects of right ventricular pacing and LBBB on left ventricular function. Br Heart J 1993; 69:166-73) 29% of patients with CHF had LBBB. Left bundle branch block delays left ventricular ejection due to delayed left ventricular activation as the electrical impulse has to travel from the right to the left side leading to sequential rather than simultaneous activation, as mentioned before. In addition, different regions of the left ventricle (LV) may not contract in a coordinated fashion.

Cardiac resynchronization, also knows as Bi-Ventricular (Bi-V) pacing, has shown beneficial results in patients with CHF and LBBB. During Bi-V pacing, both the right and the left ventricle (RV, LV) of the heart are paced simultaneously to improve heart pumping efficiency. It has also been shown recently that even some patients with no conduction system abnormalities, such as LBBB, may also benefit from the Bi-V pacing. During Bi-V pacing, in addition to the standard right atrial and right ventricular lead used in currently available defibrillators or pacemakers, an additional lead is positioned into the coronary sinus. The additional lead is then advanced into one of the branches of the coronary sinus overlying the epicardial (outer) left ventricular surface. Once all of the leads are in place, the right and left ventricular leads are paced simultaneously, thus achieving synchronization with atrial contraction.

There are, however, several problems with this approach. First, this type of procedure is time-consuming. Second, placement of the LV lead is limited to sites available that provide reasonable pacing and sensing parameters. And third, cannulating the coronary sinus may be challenging as a result of an enlarged right atrium, rotation of the heart, or presence of Tebesian valve (a valve close to the opening of the coronary sinus). Coronary sinus stenosis (occlusion) has also been reported in patients with prior coronary artery bypass surgery, further complicating the problem.

In most instances, problems with the placement of the coronary sinus lead are identified at the time of the interventional procedure. In the event of the coronary sinus lead placement procedure being abandoned, the patient is brought back to the operating room and the LV lead is positioned epicardially. During this procedure, an incision is made on the lateral chest wall and the lead is placed on the outer side of the left ventricle.

Unfortunately, there are many problems with epicardial lead placement as well, some of which include but are not limited to:

Limited view of the posterolateral area of the left ventricle using the incision of the chest wall, also called minithoracotomy;

The limited number of placement sites providing reasonable pacing and sensing parameters;

Inability to identify the most appropriate location and placement of the lead at the most appropriate site;

Potential risk of damaging the coronary arteries and venous system; and

Difficulty in identifying the ideal pacing site as a result of one or more of the above limitations.

It has also been shown that LV pacing alone may be as effective as Bi-V pacing. However, due to the unstable nature of the coronary sinus lead, a pacing and sensing lead is usually placed in the right ventricle in currently used techniques.

Cardiac CT may be used to create a roadmap of coronary sinus and left ventricular anatomy such that appropriate sites may be identified for the placement of a LV pacing lead for Bi-V/LV pacing, either at the most appropriate branch of the coronary sinus, or on the left ventricular wall epicardially (from outside). CT or MR imaging may also identify areas devoid of blood vessels and nerves, as well as scar tissue. These modalities may also be used to determine the asymmetric contraction of the ventricles and identify different regions of the ventricles not contracting in a coordinated fashion. The presence of scarring from previous heart attacks may make this uncoordinated contraction even worse.

While existing medical procedures may be suitable and appropriate for certain medical conditions, procedural limitations still exist. Accordingly, there remains a need in the art for an improved method and apparatus for registering 3D models of anatomical regions with projection images of the same to overcome these drawbacks.

BRIEF DESCRIPTION OF THE INVENTION

Embodiments of the invention include an imaging system for use in a medical intervention procedure. A first image acquisition system of a first modality employing a catheter at an anatomical region of a patient is configured to produce a first image of the anatomical region using fluoroscopy, the first image comprising a set of fluoroscopy projection images. A second image acquisition system of a second different modality is configured to generate a 3D model of the anatomical region. An anatomical reference system is common to both the first and second image acquisition systems. A processing circuit is configured to process executable instructions for registering the 3D model with the fluoroscopy image in response to the common reference system and discernible parameters associated with the catheter in both the first and second image acquisition systems.

Other embodiments of the invention include a method of registering a 3D model of an anatomical region of a patient with projection images of the same from an interventional fluoroscopy system. A fluoroscopy image of the anatomical region, which includes a catheter, is generated from the fluoroscopy system. A 3D model of the anatomical region is generated from a second image acquisition system of a different modality. The fluoroscopy image and the 3D model are analyzed with respect to a common anatomical reference system, and the 3D model is registered with the fluoroscopy image in response to the common reference system and discernible parameters associated with the catheter in both the fluoroscopy system and the second image acquisition system.

Further embodiments of the invention include a computer program product for registering a 3D model of an anatomical region of a patient with projection images of the same from an interventional fluoroscopy system. The product includes a storage medium, readable by a processing circuit, storing instructions for execution by the processing circuit for carrying out some or all portions of the aforementioned method.

BRIEF DESCRIPTION OF THE DRAWINGS

Referring now to the figures, which are exemplary embodiments, and wherein like elements are numbered alike.

DETAILED DESCRIPTION

By using the imaging capabilities of the CT and registering these images with X-ray fluoroscopy images, pulmonary veins and other areas involved with initiating and sustaining AF may be more precisely and easily isolated, thereby improving the success rate from a radiofrequency catheter procedure.

Embodiments of the invention disclosed herein provide also a system and method by which 3D models of anatomical structures, such as the coronary sinus and left ventricle for example, may be registered with fluoroscopy images, thereby allowing the pacing and/or defibrillation leads to be navigated and placed at the most appropriate site, which should assist in improving the effectiveness of Bi-V or LV pacing.

Further embodiments of the invention include using the motion of the catheter placed in the coronary sinus to help appropriate registration and to determine and synchronize the movement of the 3D model of the heart chamber with the catheter movement.

In accordance with embodiments of the invention, image registration is performed not by aligning anatomical structures that are depicted by the two modalities, but by aligning the anatomical structures with a tool placed by the physician in an anatomical structure. In an exemplary embodiment, the tool is a catheter that may be placed in the coronary sinus, or a lead that may be placed in one of the heart chambers, such as the right ventricle for example. Another aspect of the invention involves using the motion of the catheter in the coronary sinus to determine the motion of the heart and to register the anatomical structure in the same phase as the computed tomography (CT) is segmented to reconstruct the 3D model of the anatomical structure.

A detailed description of embodiments of the invention is presented herein by way of exemplification and not limitation with reference to the several figures.

Figure 1:
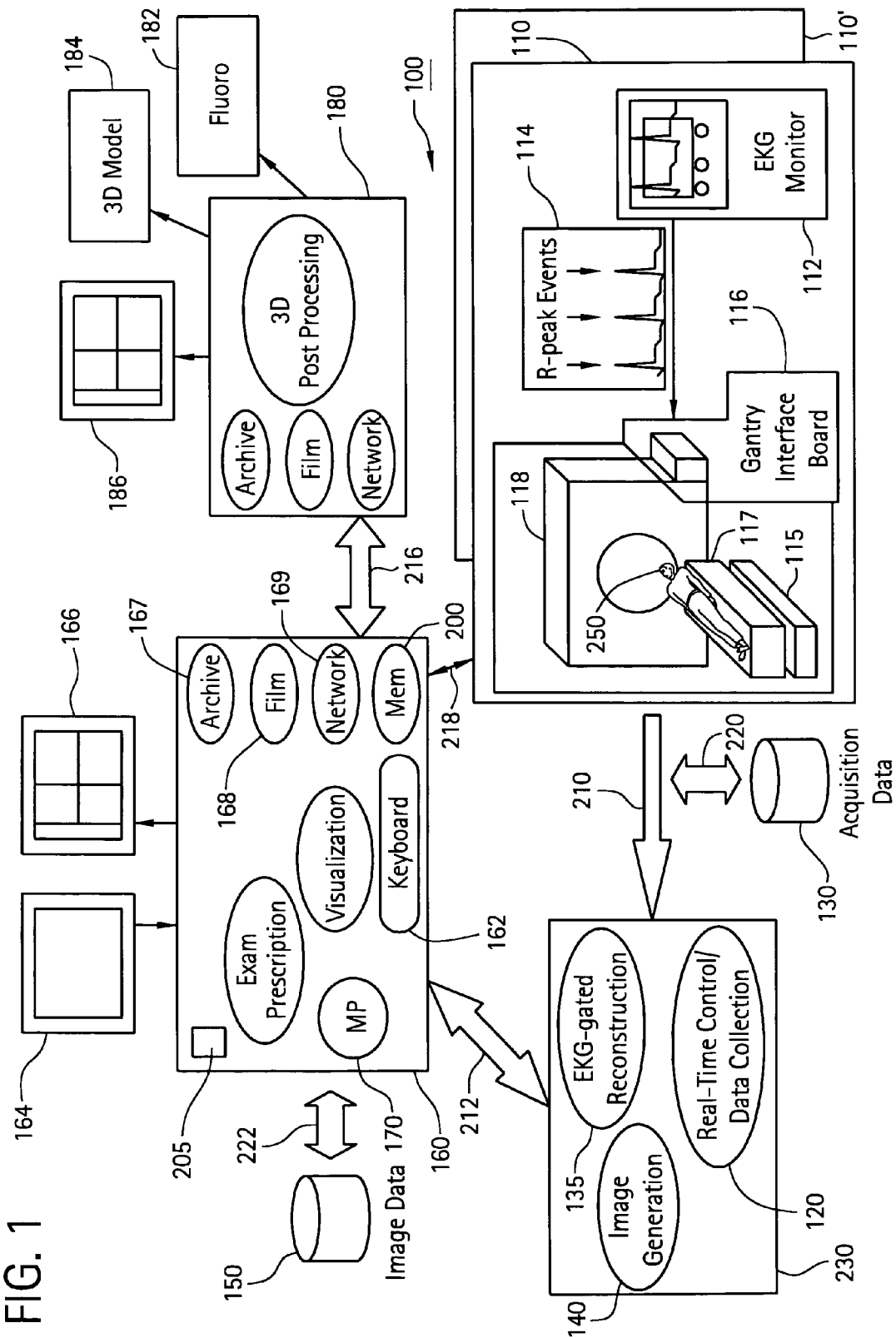
FIG. 1 depicts a generalized schematic of an imaging system for use in a medical intervention procedure.

FIG. 1 depicts a generalized schematic of an imaging system 100 for use in a medical intervention procedure, such as, for example, an atria fibrillation ablation procedure, or a bi-ventricular procedure, for example. In an embodiment, the imaging system 100 includes: an imaging apparatus 110 for generating cardiac image data, such as, for example, image data of the left atrium and the coronary sinus, a data acquisition system 120 for acquiring the cardiac image data from imaging apparatus 110, an acquisition database 130 for storing the cardiac image data from data acquisition system 120, an image generation system 140 for generating a viewable image from the cardiac image data stored in acquisition database 130, an image database 150 for storing the viewable image from image generation system 140, an operator interface system 160 for managing the imaging apparatus 110 and the cardiac image data and viewable image in databases 130, 150, which may be combined into one database, and a processing system 180 for analyzing and displaying the viewable image in database 150 and being responsive to operator interface system 160. Processing software in processing system 180 includes instructions, and is therefore adapted, to analyze data and display images, thereby converting processing system 180 from a general processor into a specialized processor. Scanned data that is capable of being converted into a viewable image is referred to herein as image data.

System communication links 210, 212, 216, 218 and database communication links 220, 222 provide a means for signal communication amongst and between systems 110, 120, 140, 160, 180 and databases 130, 150. Communication links 210-222 may be hardwired or wireless. Operator interface system 160 may be a standalone input/output terminal or a computer including instructions in a variety of computer languages for use on a variety of computer platforms, such as but not limited to, for example, DOS™-based computer systems, Apple™-based computer systems, Windows™-based computer systems, HTML-based computer systems, specialized program language-based computer systems, or the like.

Operator interface system 160 includes a processor 170, such as, for example, a microprocessor (MP) or any other processing circuit suitable for the purposes disclosed herein, for managing the imaging apparatus 110, for managing the data acquisition and image generation systems 120, 140, for processing and managing the information in acquisition and image databases 130, 150, and for managing the processing at processing system 180. Operator interface system 160 also includes: a memory 200 that contains specific instructions relating to medical scanning procedures, user input means, such as, for example, a keyboard 162, and user output means, such as, for example, displays 164, 166. In an embodiment, interface system 160 and processing system 180 may be integrally arranged. Display 164 may be adapted for exam prescription, and display 166 may be adapted for visualization. Alternatively, displays 164 and 166 may be integrated into one display. Exam prescription includes such input parameters as: CT scan or region of scan control, fluoroscopy system control, data acquisition control, and the like. Operator interface system 160 may also be employed during an actual interventional procedure to display both fluoroscopy images and 3D CT images, as discussed below. During an actual medical interventional procedure, data port 205 accepts information from a medical probe, such as, for example, a catheter 260, thereby permitting data analysis in a real-time fashion during the actual interventional procedure.

Imaging apparatus 110 includes an electrocardiogram (EKG) monitor 112 that outputs R-peak events 114, which generally delineate the beginning of a heart cycle, through an interface board (patient interface unit) 116 into a scanner 118, such as a CT scanner for example, a fluoroscopy system 115, and a patient table 117. Scanner 118 and fluoroscopy system 115 are alternatively herein referred to as image acquisition systems. The interface board 116 enables synchronization between the scanner data and the EKG monitor data. Alternatively, the interface board 116 may be used to couple the EKG monitor 112 to the scanner 118. An example of an interface board 116 is a Gantry interface board. An exemplary scanner 118 is a cardiac computed tomography (CT) system with support for cardiac imaging. ECG gated reconstruction followed by segmentation reconstruction of 3D models (in diastolic phase) allows imaging of the heart free of motion. During sinus rhythm, segmentation reconstruction will be done at 75% of cardiac cycle (in diastole). Phase location is selected at around 45% of the cardiac cycle where the patient is in atria fibrillation. This phase is chosen as the R-R intervals are shorter. However, the illustrated scanner 118 is for exemplary purposes only; other imaging systems known in the art may also be used. Examples of other imaging systems include, but are not limited to, X-ray systems (including both conventional and digital or digitized imaging systems), magnetic resonance (MR) systems, positron emission tomography (PET) systems, ultrasound systems, nuclear medicine systems, and 3D fluoroscopy systems. Imaging apparatus 110 may have both a scanner 118 and a fluoroscopy system 115 for use as disclosed here, or imaging system 100 may have two imaging apparatuses 110, 110', with imaging apparatus 110 having a CT scanner 118, and imaging apparatus 110' having a fluoroscopy system 115. Fluoroscopy system 115 is also herein referred to as an interventional system or a first image acquisition system, and CT scanner 118 is also herein referred to as a 3D model system or a second image acquisition system.

Figure 2:
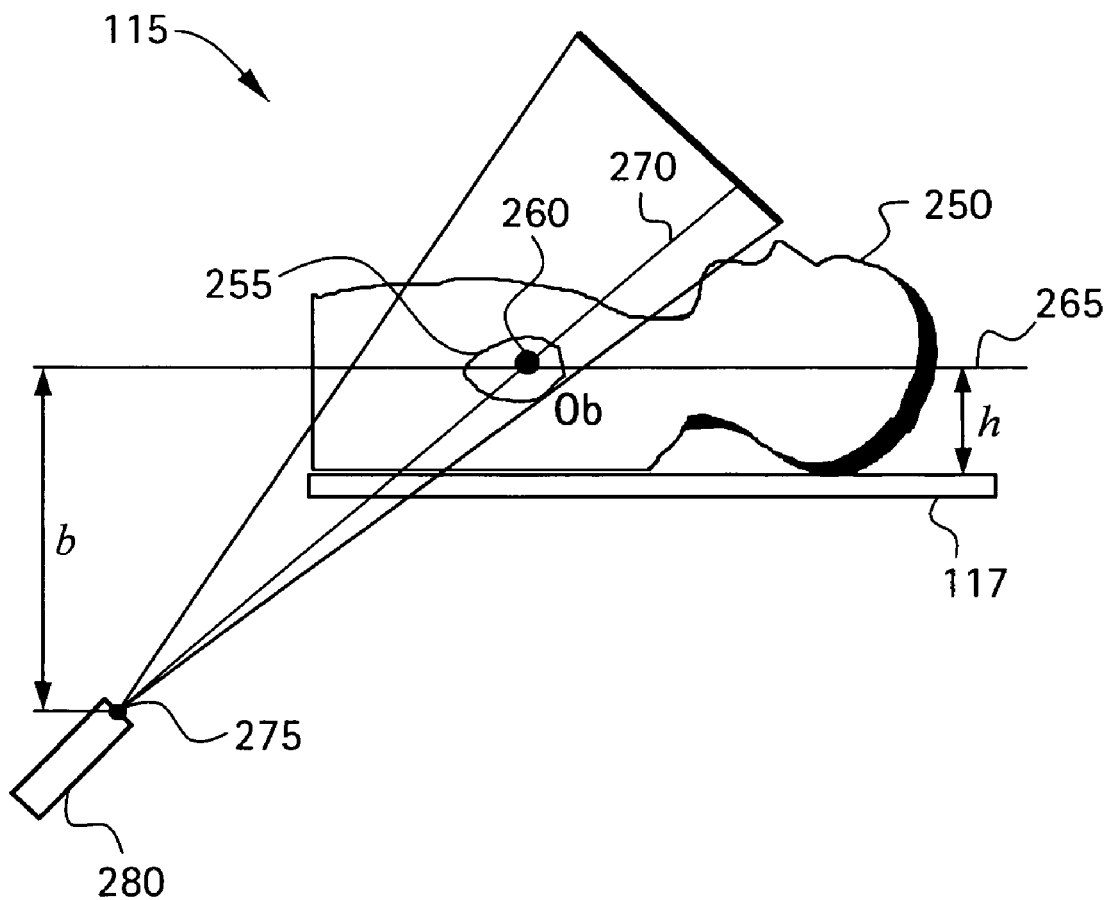
FIG. 2 depicts an expanded view of a portion of the system of FIG. 1.

FIG. 2 depicts an interventional system 115 where a patient 250 on table 117 has a catheter 260 placed within an anatomical region 255, such as the coronary sinus in the patient's heart for example. In an embodiment, catheter 260 is positioned at a known anatomical structure in the anatomical region (such as the coronary sinus at the heart) at a location defined by the intersection of a horizontal plane 265 and the line 270 joining the focal point 275 of the x-ray source 280 of the fluoroscopy system 115 to the projection of the catheter 260. Other anatomical regions may include a heart chamber, such as right ventricle for pacing/defibrillation lead in bi-ventricular pacing, or a pulmonary vein for example, and other anatomical structures may include a mitral valve, a pulmonary vein ostia, a junction into an atria, or a junction into a ventricle, for example. However, embodiments of the invention are not intended to be limited to only those anatomical regions and structures disclosed herein. In an exemplary embodiment, the location of the horizontal plane 265 is defined by an elevation h above the anatomical reference system (table) 117 to the known anatomical structure (coronary sinus) at the anatomical region (heart) 255. In this manner, a known location of the catheter 260 in the fluoroscopy system 115 and the 3D model system 118 may be established.

Referring back to FIG. 1, imaging apparatus 110 also includes EKG gated acquisition or image reconstruction 135 capabilities to image the heart free of motion, typically in its diastolic phase. Interfacing with EKG monitor 112 allows real time acquisition of the cardiac electrical impulses and allows gated acquisition or retrospective reconstruction of the acquired data. As mentioned previously during sinus rhythm for example it could be 75% and during atria fibrillation at about 45% due to shorter R-R intervals. This allows elimination of the cardiac motion by imaging the heart in the same phase of the diastole. The acquired data may be stored on a database or used to generate the required image by using one or more protocols optimized for imaging. In an embodiment, the image data stream from image generation system 140 is communicated via link 212 to the operator interface system 160 for display and visualization, and communication link 216 to processing system 180. The image data used by software at operator interface system 160 for exam prescription and visualization may be stored in image database 150. The imaged data may be archived 167, put on a film 168, and/or sent over a network 169 to processing system 180 for analysis and review, including 3D post-processing. The 3D model image 184 and the fluoroscopy image 182 may be viewed singly or in combination on display 186. In the case of AF planning, post-processing software at processing system 180 allows detailed 3D and endocardial views of the left atrium and pulmonary veins. These images and others may be stored and viewed at the time of the interventional procedure.

Imaging apparatus 110 further includes circuitry for acquiring image data and for transforming the data into a useable form, which is then processed to create a reconstructed image of features of interest within the patient. The image data acquisition and processing circuitry is often referred to as a "scanner", regardless of the type of imaging system, because some sort of physical or electronic scanning often occurs in the imaging process. The particular components of the system and related circuitry differ greatly between imaging systems due to the different physics and data processing requirements of the different system. However, it will be appreciated that the present invention can be applied regardless of the selection of a particular imaging system.

Data is output from imaging apparatus 110 into subsystem 230, which includes software to perform data acquisition in data acquisition system 120 and image generation in image generation system 140. Data control is either provided by operator interface system 160 or within subsystem 230 via communication link 212. Data that is output from the imaging apparatus 110, including R-peak events 114, is stored in the acquisition database 130. Data acquisition in system 120 is performed according to one or more acquisition protocols that are optimized for imaging the heart, and specifically for imaging the right atrium and/or coronary sinus.

In an exemplary embodiment, the 3D image data of the atrium is created using a protocol that is optimized for the left atrium, such as coronary artery imaging protocol or CardEP protocol for example. Exemplary parameters used in these protocols include 0.5 second Gantry periods with 0.375 helical pitch factors, 120 kilovolts, 250 milliamps and 0.625 or 1.25 mm (millimeter) slice thickness. These functions may be performed with commercially available off the shelf software tools, such as Advanced Vessel Analysis (AVP) or CardEP for example. After the above mentioned tools are applied to the image data, further processing may be applied, such as thresholding, floater filtering, and scalping, for example. These processes are used to clean up the images and may be automated. Automated processes may require queues from the operator as the operator is stepped through the process by the operating software. Following the image clean up process, the remaining cardiac chambers are eliminated and only the left atrium is visualized. A detailed 3D image of the left atrium and the pulmonary veins may then be created. The 3D and endocardial (view from inside) are visualized using volume rendering techniques using a variety of volume rendering commercially available software packages, such as VR and Cardiac Image Quality (CARDIQ) for example. Once the 3D images are created, the 3D model geometry then needs to be registered with that of the fluoroscopy system.

Registration is the process of aligning images. Intra-subject multi-modality registration is registration of two different modalities in the same patient. The number of parameters needed to describe a Transformation (Registration) is referred to herein as number of "Degrees of Freedom". An assumption is made that the 3D model behaves as a rigid body, as the anatomy of the anatomical structure being registered has not changed significantly. In this case, 3 translations and 3 rotations, which give 6 degrees of freedom, will lead to a successful registration. Each device used for registration needs to be calibrated to approximate the size of the anatomical 3D model. This requires 3 extra degrees of freedom equating to "scaling" in each direction. If a set of corresponding anatomical landmarks (fiducials) x and y can be identified, then the registration can be affected by selecting a transformation that will align these areas. Each view in the device being used is being referred to as the co-ordinate system that will define a space in that view. Successful registration will involve the determination of a Transformation between the fiducials in one space (X) of one view, for example, with that of another space (Y), for example. Successful registration will involve determination of a Transformation T between fiducials in the "X" space with those in the "Y" space that minimizes the error $T(x)-y$, where $T(x)=Rx+t$, R is the Rotation, and t is the translation.

A Transformation matrix defines how to map points from one co-ordinate space into another co-ordinate space. By identifying the contents of the Transformation matrix, several standard operations, including rotation, translation and scaling, can be performed.

There may be significant difficulty in identifying and aligning anatomical landmarks in two co-ordinate spaces for successful registration. Instead of aligning anatomical structures, a unique feature of the present invention involves registration performed by aligning the anatomical structures with a tool placed by the physician in the anatomical structure. Although other tools such as a lead can be placed in an anatomical structure, such as the right ventricle in the case of bi-ventricular pacing for example, the embodiment disclosed herein uses a catheter placed in the coronary sinus.

Another embodiment of the invention involves registration of the fluoroscopic image with the 3D model of the anatomical structure. As depicted in FIGS. 4 A, B and C, which are discussed in more detail below, the coronary sinus catheter positioned in the coronary sinus can be clearly seen on the fluoroscopic projection image. The fluoroscopy image can be also used as an interventional system to locate the mapping and ablation catheter and or/pacing lead as it is navigated to the appropriate site. A further embodiment of the invention involves using the motion of the coronary sinus catheter to determine the phase of the heart motion. Apart from assessing the continuous movement of the chamber, such as the left atrium, the motion of the catheter can also be used to perform registration of the same phase of diastole (75% of cardiac cycle for example) where the CT image is being reconstructed.

FIGS. 5 A, B, C, D, E and F, have been used for validation of the registration process performed in accordance with an embodiment of the invention by the injection of contrast in one of the pulmonary veins. As illustrated, FIGS. 5 A, B, C, D, E and F, depict injection of a contrast in the Right superior pulmonary vein (RSPV) through a sheath placed in the RSPV. The contrast is injected after the registration is completed to assess accuracy of registration. In FIG. 5A, there is no contrast, while FIG. 5B shows injection of the contrast followed by a gradual washout as shown in subsequent FIGS. 5 C, D and E. In FIG. 5 F, no more contrast is seen, suggesting that it has washed out completely. While not specifically delineated, it has been demonstrated that the contrast filled RSPV nicely superimposes on the RSPV shown on the registered CT image, suggesting an accurate registration.

The image formation model of the fluoroscopy system is a conic projection. The location of the center of the projection and the position of the imaging plane are in principle well described with respect to an anatomical reference system, such as the patient table 117 for example. This anatomical reference system 117 is coherent with that used to position the 3D model obtained from the CT system 118.

Assuming that an established protocol is followed by an operating technician during the positioning of the patient in the two acquisition systems, that is, the fluoroscopy system 115 and the CT system 118, the anatomical reference system 117 may then be considered common to both acquisitions systems, especially in terms of orientation, that is, rotation between the two reference systems may be considered negligible.

As previously mentioned, and to provide for the registration of the 3D model image 184 with the fluoroscopy image 182, a catheter 260 (depicted in-situ in FIG. 4) is employed during the operation of fluoroscopy system 115, which will now be described with reference to FIG. 3 in combination with FIGS. 1 and 2. As an important aside, however, it should be noted that the geometrical structure of the catheter 260 may not be sufficiently rich enough to allow a complete registration of the two modalities without employing embodiments of the invention disclosed herein. For example, and in the case of coronary imaging, a scaling factor computed only from the established relationship between the superior or inferior vena cava (SVC, IVC) and the coronary sinus (CS) in conjunction with the catheter 260 inside the CS, may not be precise enough for accurate registration.

Figure 4A:
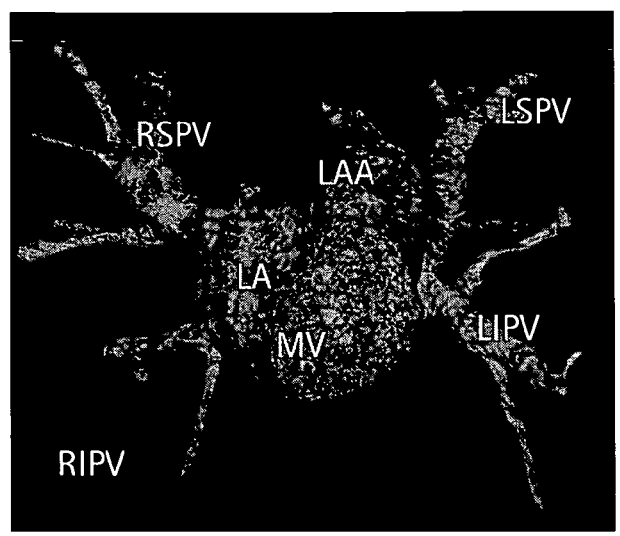
FIGS. 4 A, B and C, depict an exemplary registration of a 3D model with a fluoroscopy image in accordance with an embodiment of the invention.
Figure 4B:
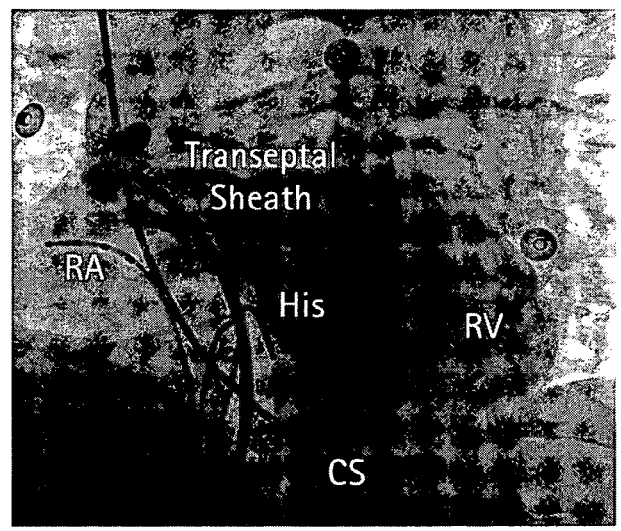
Figure 4C:
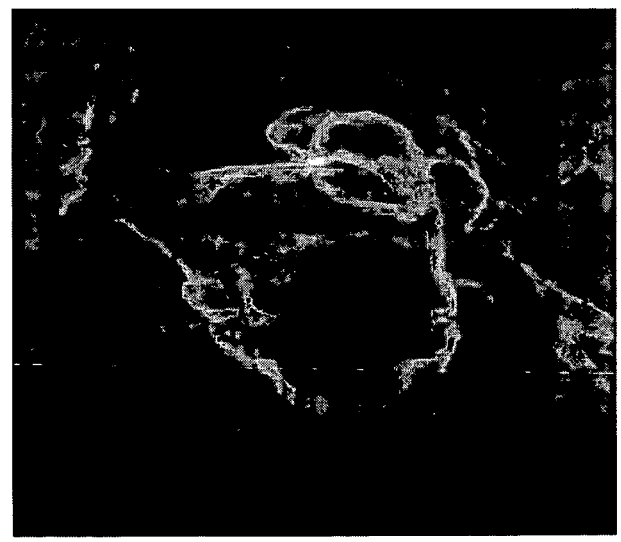
Figure 5A:
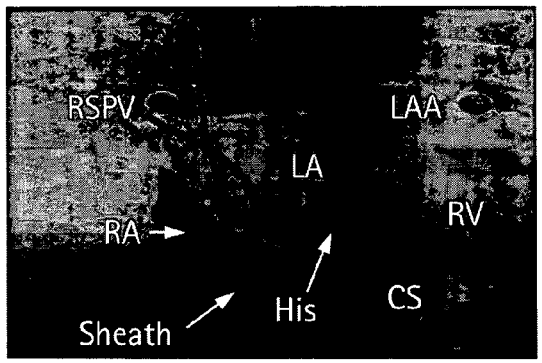
FIGS. 5 A, B, C, D, E and F, depict validation of the registration process performed in accordance with an embodiment of the invention.
Figure 5B:
Figure 5C:
Figure 5D:
Figure 5E:
Figure 5F:
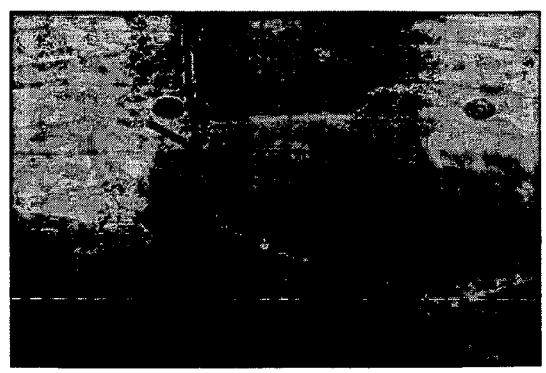

In FIG. 4A, the 3D model of the left atrium obtained using CT imaging and segmentation in anteroposterior (AP) view is depicted. In FIG. 4B, a projection image of the heart obtained using fluoroscopy system is depicted, where multiple catheters including the coronary sinus catheter are positioned at different locations by the physician. As can be appreciated, there is little or no contrast differentiation between the different structures in the fluoroscopic image. In FIG. 4C, a registered image using the 3D model of the left atrium and the projection image using the fluoroscopy is depicted. Referring to FIGS. 4A, B and C collectively, which are all depicted in anteroposterior view, catheter 260 is located in the coronary sinus (CS Catheter), the left atrial appendage is designated LAA, the right superior pulmonary vein is designated RSPV, the left superior pulmonary vein is designated LSPV, and the mitral valve annulus is designated MV.

Figure 3:
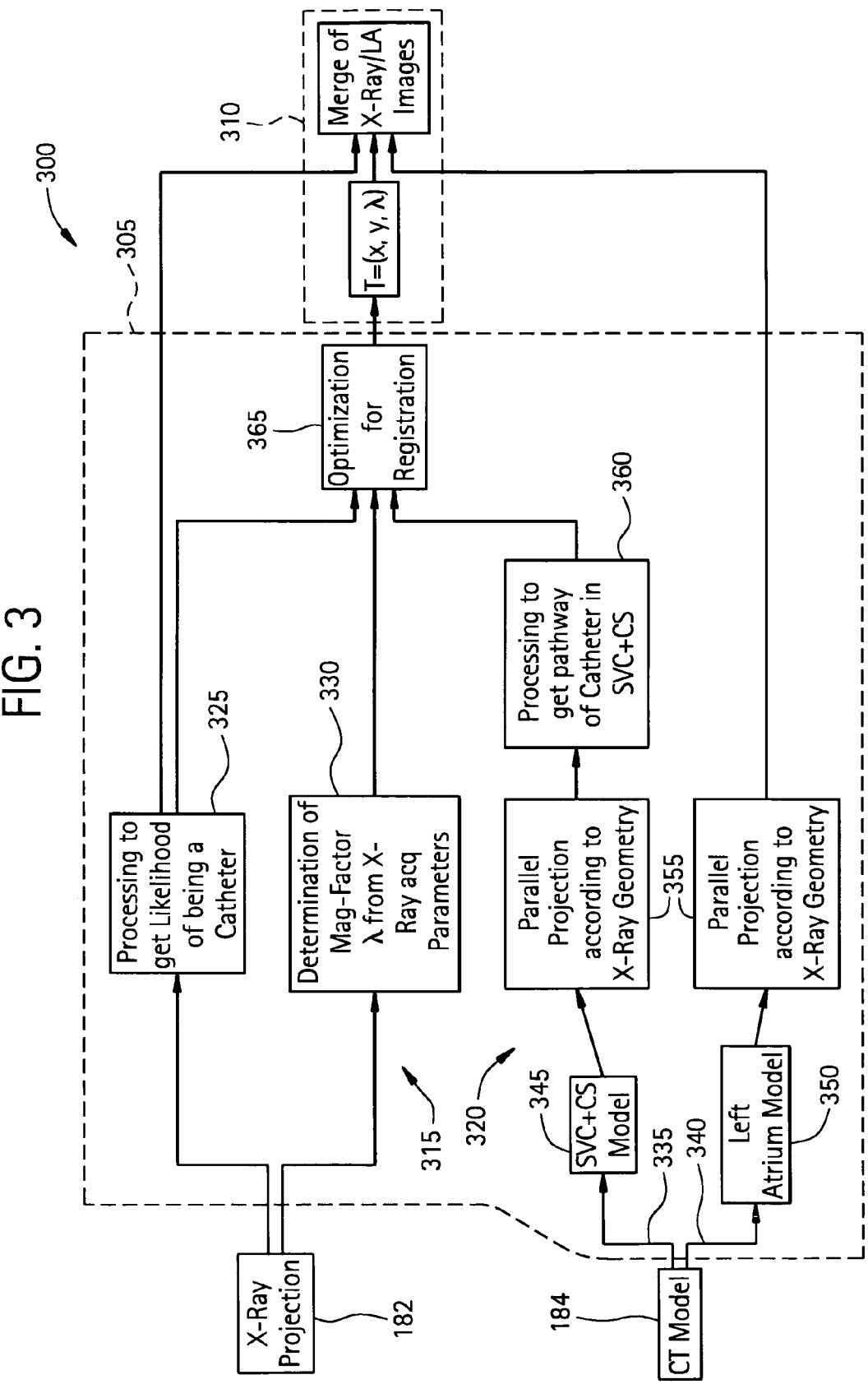
FIG. 3 depicts a generalized flowchart of a process for implementing an embodiment of the invention using the imaging system of FIG. 1.

FIG. 3 depicts a flowchart of an exemplary method 300 for registering 3D model image 184 with fluoroscopy image 182, where fluoroscopy system 115 is used to generate 2D fluoroscopy images (such as x-ray projection images) 182, and CT system 118 is used to generate 3D model images 184. Prior to image acquisition, catheter 260 is placed at an anatomical structure (such as the coronary sinus) of an anatomical region (such as the heart) 255 of patient 250 using known techniques. During the acquisition of images 182, 184, a common anatomical reference system (such as the patient table) 117 is used, thereby establishing a referential link between the two imaging systems 115, 118. After image acquisition, processing circuit 170 processes 305 the image data 182, 184 in such a manner, to be discussed in more detail later, as to result in 3D model 184 being registered 310 with fluoroscopy image 182. In general, processing circuit 170 utilizes the common reference system 117 to link known geometric information between and pertaining to each image acquisition system 115, 118, and uses discernible parameters associated with catheter 260 that are available from both the first and second image acquisition systems 115, 118, in order to register the two images 182, 184.

During the processing phase 305, pre-processing 315, 320 on images 182, 184, respectively, takes place prior to the actual registration process 310. During pre-processing 315, the x-ray projection images 182 are analyzed 325, 330 to determine the likelihood of the apparent catheter image actually being the catheter 260, and to determine a magnification factor λ for the x-ray image 182 based on the known actual catheter size, measured prior to insertion into the patient 250, and the apparent catheter size, measured from the x-ray image 182.

Pre-processing 320 follows both paths 335, 340, where path 335 relates to the processing of the anatomical structures in the CT model used for registration, and path 340 relates to the processing of the clinical structure that is desired to be displayed following registration. In accordance with embodiments of the invention, at least one catheter is disposed in the superior vena cava SCV and/or coronary sinus CS. In either path 335, 340, pre-processing 320 performs a parallel projection operation 355 on the 3D model 184 with respect the geometry discernible from the fluoroscopy image 182, thereby properly orienting the 3D model 184 with respect to the fluoroscopy image 182. At block 360, image 184 is processed to establish the pathway of the catheter 260 in the vessel or vessels of interest, such as the SVC or coronary sinus. At block 365, the result of the processing done at 325 and 330 is used to register the images 182 with the pathway 360. As a result of this registration, a transformation is identified that links the images 184 and images 182.

At block 310, the registration process involves generating both a translation factor (x, y) for translating the 3D model 184 with respect to the fluoroscopy image 182, and a scaling factor λ for adjusting the scale of the 3D model 184 with respect to the fluoroscopy image 182. The translation factor is straightforward, and uses known techniques and processes, such as aligning the centers of common anatomical structures for example. In principle, the alignment method can also compensate for a rotation along an axis perpendicular to the projection plane. However, the scaling factor is not so straightforward and will now be described by way of alternative examples. In general, however, the scaling factor is dependent on known information from the common anatomical reference system 117 and discernable features of the catheter 260.

In a first embodiment, the apparent diameter of the catheter 260 in the fluoroscopy image 182 is determined and then compared with the known actual diameter of the catheter 260. From this information, the actual dimension of an anatomical structure in the anatomical region 255 in the fluoroscopy image 182 may be determined. The anatomical structure in the fluoroscopy image 182 is then matched with the same anatomical structure in the 3D model 184, where now the actual and apparent sizes of the same anatomical structure in the 3D model 184 may be compared. From this comparison, a scaling factor may be established between the first and second image acquisition systems 115, 118.

In a second embodiment, the catheter 260 is disposed at a known anatomical structure in the anatomical region 255 at a location defined by the intersection of a horizontal plane 265 and the line 270 joining the focal point 275 of the fluoroscopy system 115 to the projection of the catheter 260 in the fluoroscopy image 182. Here, the horizontal plane 265 is defined by an elevation h above the anatomical reference system 117 to the known anatomical structure in the fluoroscopy system 115, which establishes a known location of the catheter 260 in the fluoroscopy system 115 and the CT system 118 relative to the anatomical reference system 117. Knowing the location of the catheter 260 in the 3D model 184 and the actual and apparent dimensions for elevation h in the 3D model 184, the actual size of the same anatomical structure in the 3D model 184 as that in the fluoroscopy image 182 may be determined. By comparing the actual and apparent sizes of the anatomical structure in the 3D model 184, a scaling factor between the first and second image acquisition systems 115, 118 may be established.

In a third embodiment, the fluoroscopy system 115 is used to produce a first and a second set of fluoroscopy projection images, which are generated using at least two different x-ray projections separated by an angle sufficient to produce discernibly different projection images of the anatomical region 255. Here, as in other embodiments, the catheter 260 is disposed at a known anatomical structure in the anatomical region 255. By analyzing the two sets of projection images using a known triangulation approach, the location of the catheter 260 in the 3D model 184 with respect to the focal point 275 of the x-ray source 280 of the fluoroscopy system 115 may be determined, thereby defining a dimension b, which establishes a known location of the catheter 260 in the fluoroscopy system 115 and the CT system 118 relative to the focal point 275. Knowing the location of the catheter 260 in the 3D model 184 and the actual and apparent dimensions for dimension b in the 3D model 184, the actual size of the same anatomical structure in the 3D model 184 as that in the fluoroscopy image 182 may be determined. By comparing the actual and apparent sizes of the anatomical structure in the 3D model 184, a scaling factor between the first and second image acquisition systems 115, 118 may be established.

While exemplary embodiments disclosed herein reference the size of the catheter 260 for scaling purposes, it will be appreciated that other measurable features may also be used for scaling, such as the interelectrode distance at the catheter 260, for example. Accordingly, embodiments of the invention are not intended to be limited to only a reference to the size of catheter 260 for scaling purposes.

To avoid possible jitter of the registered image of the 3D model 184 due to cyclical movement of the heart, or other anatomical region 255 of interest, the processing circuit 170 may be responsive to additional executable instructions for registering the 3D model 184 with the fluoroscopy image 182 in synchronization with the cyclical movement of the anatomical region 255, that is, in synchronization with the cyclical movement of a heart beat.

While embodiments of the invention disclose a heart as an exemplary anatomical region, it will be appreciated that the invention is not so limited and that the scope of the invention includes other anatomical regions of interest within the patient. While embodiments of the invention disclose a coronary sinus as an exemplary anatomical structure within an anatomical region, it will be appreciated that the invention is not so limited and that the scope of the invention includes other anatomical structures within an anatomical region. While embodiments of the invention disclose a catheter placed within the patient, it will be appreciated that the invention is not so limited and that the scope of the invention includes other devices discernable via x-ray and CT, such as a pacing lead for example.

An embodiment of the invention may be embodied in the form of computer-implemented processes and apparatuses for practicing those processes. The present invention may also be embodied in the form of a computer program product having computer program code containing instructions embodied in tangible media, such as floppy diskettes, CD-ROMs, hard drives, USB (universal serial bus) drives, or any other computer readable storage medium, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein when the computer program code is loaded into and executed by a computer, the computer becomes an apparatus for practicing the invention. When implemented on a general-purpose microprocessor, the computer program code segments configure the microprocessor to create specific logic circuits. The technical effect of the executable instructions is to register a 3D model with a fluoroscopy image for at least the purpose of assisting in a medical intervention procedure.

As disclosed, some embodiments of the invention may include some of the following advantages: the availability of a CT-Fluoro registration technique that will allow pacing leads to be navigated and placed at the most appropriate site, thereby improving the effectiveness of bi-ventricular or left ventricle pacing; the availability of a CT-Fluoro registration technique that will show the location of the coronary sinus on the 3D model, thereby eliminating the need in bi-ventricular pacing to perform coronary sinus angiography prior to implantation of the coronary sinus lead; the ability to use the right ventricular lead in atrial fibrillation ablation for continuous registration; for a given orientation of the interventional system, the ability to automatically generate a projection of the 3D model that is geometrically close to the image provided by the interventional system; the ability to merge the information obtained from a 3D model generated using a scanner with the real-time live information provided by fluoroscopy imaging; and, the availability of a technique that will allow visualization of the true 3D geometry of the different pulmonary vein-left atrial junction and other strategic areas in the atria by using imaging capabilities of the CT, and more importantly registering these images with X-ray fluoroscopy, to help isolate the pulmonary veins and these areas which initiate and sustain AF more precisely and easily.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

The invention claimed is:

1. An imaging system for use in a medical intervention procedure, comprising:
    a first image acquisition system of a first modality employing a catheter at an anatomical region of a patient and configured to produce a first image of the anatomical region using fluoroscopy, the first image comprising a set of fluoroscopy projection images;
    a second image acquisition system of a second different modality configured to generate a 3D model of the anatomical region;
    an anatomical reference system common to both the first and second image acquisition systems; and
    a processing circuit configured to process executable instructions for registering the 3D model with the fluoroscopy image in response to the common reference system and discernible parameters associated with the catheter in both the first and second image acquisition systems.

2. The imaging system of claim 1, wherein the processing circuit is further configured to process executable instructions for:
    generating a translation factor for translating the 3D mode with respect to the fluoroscopy image;
    optionally registering the 3D model and the fluoroscope image in the same phase of a cardiac cycle;
    optionally rotating the 3D model about an axis perpendicular to the projection plane of the fluoroscopy projection image; and
    generating a scaling factor for adjusting the scale of the 3D model with respect to the fluoroscopy image, the scaling factor being dependent on a discernable feature of the catheter.

3. The imaging system of claim 2, wherein:
    the anatomical region is a heart of the patient; and
    the processing circuit is further configured to process executable instructions for registering the 3D model with the fluoroscopy image in synchronization with cyclical movement of the heart using a catheter placed in the heart.

4. The imaging system of claim 3, wherein the anatomical region comprises a heart, and the cyclical movement of the anatomical region comprises a heart beat.

5. The imaging system of claim 2, wherein the catheter has a known actual diameter, and wherein the processing circuit is further configured to process executable instructions for:
    determining the apparent diameter of the catheter in the fluoroscopy image, comparing the apparent diameter of the catheter with the known actual diameter of the catheter, determining in response thereto an actual dimension of an anatomical structure in the anatomical region in the fluoroscopy image, matching the anatomical structure in the fluoroscopy image with the same anatomical structure in the 3D model, comparing the actual and apparent sizes of the same anatomical structure in the 3D model, and generating therefrom a scaling factor between the first and second image acquisition systems.

6. The imaging system of claim 2, wherein:
    the catheter is disposed at a known anatomical structure in the anatomical region at a location defined by the intersection of a horizontal plane and the line joining the focal point of the fluoroscopy system to the projection of the catheter, the horizontal plane being defined by an elevation h above the anatomical reference system to the known anatomical structure in the fluoroscopy system, thereby establishing a known location of the catheter in the first and second image acquisition systems; and
    the processing circuit is further configured to process executable instructions for:
    determining the actual size of the same anatomical structure in the 3D model in response to the known location of the catheter in the 3D model and the elevation h, comparing the actual and apparent sizes of the anatomical structure in the 3D model, and generating therefrom a scaling factor between the first and second image acquisition systems.

7. The imaging system of claim 2, wherein:
    the first image acquisition system is further configured to produce a second set of fluoroscopy projection images, the first and second sets of projection images being generated by at least two different x-ray projections separated by an angle sufficient to produce discernibly different projection images of the anatomical region, the catheter being disposed at a known anatomical structure in the anatomical region; and
    the processing circuit is further configured to process executable instructions for:
    determining the location of the catheter in the 3D model with respect to the focal point of the fluoroscopy system to define a dimension b by analyzing the two sets of projection images using a triangulation approach; and
    determining the actual size of the same anatomical structure in the 3D model in response to the known location of the catheter in the 3D model and the dimension b, comparing the actual and apparent sizes of the anatomical structure in the 3D model, and generating therefrom a scaling factor between the first and second image acquisition systems.

8. The imaging system of claim 1, wherein:
the anatomical region comprises a heart, a heart chamber, a pulmonary vein, or any combination comprising at least one of the foregoing.

9. The imaging system of claim 5, wherein:
the anatomical structure comprises a coronary sinus, a mitral valve, a pulmonary vein ostia, a junction into an atria a junction into a ventricle, a ventricle, or any combination comprising at least one of the foregoing.

10. The imaging system of claim 1, wherein:
the first image acquisition system comprises an interventional fluoroscopy system; and
the second image acquisition system comprises at least one of a CT system, a MR system, an Ultrasound system, a 3D fluoroscopy system, and a PET system.

11. The imaging system of claim 1, further comprising:
an electrocardiogram (ECG) in signal communication with the patient's heart; and
a patient interface unit configured to synchronize movement of the catheter disposed at a coronary sinus with the ECG to determine the heart cycle phase of each frame from the second image acquisition system;
wherein the coronary sinus catheter movement is used to enable registration of the 3D model in the same phase as a reconstruction of the anatomical structure from the second image acquisition system.

12. A method of registering a 3D model of an anatomical region of a patient with projection images of the same from an interventional fluoroscopy system, the method comprising:
generating a fluoroscopy image of the anatomical region from the fluoroscopy system, the anatomical region including a catheter;
generating a 3D model of the anatomical region from a second image acquisition system of a different modality;
analyzing the fluoroscopy image and the 3D model with respect to a common anatomical reference system; and
registering the 3D model with the fluoroscopy image in response to the common reference system and discernible parameters associated with the catheter in both the fluoroscopy system and the second image acquisition system.

13. The method of claim 12, further comprising:
generating a translation factor for translating the 3D model with respect to the fluoroscopy image;
optionally rotating the 3D model about an axis perpendicular to the projection plane of the fluoroscopy projection image; and
generating a scaling factor for adjusting the scale of the 3D model with respect to the fluoroscopy image, the scaling factor being dependent on a discernable feature of the catheter.

14. The method of claim 12, wherein the registering comprises:
registering the 3D model with the fluoroscopy image in synchronization with cyclical movement of the anatomical region.

15. The method of claim 14, wherein the anatomical region comprises a heart, and the cyclical movement of the anatomical region comprises a heart beat.

16. The method of claim 13, wherein the catheter has a known actual diameter, and the generating a scaling factor comprises:
determining the apparent diameter of the catheter in the fluoroscopy image, comparing the apparent diameter of the catheter with the known actual diameter of the catheter, determining in response thereto an actual dimension of an anatomical structure in the anatomical region in the fluoroscopy image, matching the anatomical structure in the fluoroscopy image with the same anatomical structure in the 3D model, comparing the actual and apparent sizes of the same anatomical structure in the 3D model, and generating therefrom a scaling factor between the fluoroscopy system and the second image acquisition system.

17. The method of claim 13, wherein the catheter is disposed at a known anatomical structure in the anatomical region at a location defined by the intersection of a horizontal plane and the line joining the focal point of the fluoroscopy system to the projection of the catheter, the horizontal plane being defined by an elevation h above the anatomical reference system to the known anatomical structure in the fluoroscopy system, thereby establishing a known location of the catheter in the first and second image acquisition systems, and wherein the generating a scaling factor comprises:
determining the actual size of the same anatomical structure in the 3D model in response to the known location of the catheter in the 3D model and the elevation h, comparing the actual and apparent sizes of the anatomical structure in the 3D model, and generating therefrom a scaling factor between the fluoroscopy system and the second image acquisition system.

18. The method of claim 13, further comprising:
generating a second fluoroscopy image of the anatomical region, the first and second fluoroscopy images being generated by at least two different x-ray projections separated by an angle sufficient to produce discernibly different sets of projection images of the anatomical region, the catheter being disposed at a known anatomical structure in the anatomical region;
determining the location of the catheter in the 3D model with respect to the focal point of the fluoroscopy system to define a dimension b by analyzing the two sets of projection images using a triangulation approach; and
determining the actual size of the same anatomical structure in the 3D model in response to the known location of the catheter in the 3D model and the dimension b, comparing the actual and apparent sizes of the anatomical structure in the 3D model, and generating therefrom a scaling factor between the fluoroscopy system and the second image acquisition system.

19. The method of claim 16, wherein the anatomical structure comprises a coronary sinus, a mitral valve, a pulmonary vein ostia, a junction into an atria, a junction into a ventricle, or any combination comprising at least one of the foregoing.

20. The method of claim 12, wherein the second image acquisition system comprises at least one of a CT system, a MR system, an Ultrasound system, a 3D fluoroscopy system, and a PET system.

21. The method of claim 12, further comprising:
localizing at least one of a catheter and a lead over the registered image, thereby enabling a check of the accuracy of the registration.

22. The method of claim 12, further comprising:
injecting contrast in an anatomical structure, thereby enabling a check of the accuracy of the registration.

23. A computer program product for registering a 3D model of an anatomical region of a patient with projection images of the same from an interventional fluoroscopy system, the product comprising:

a storage medium, readable by a processing circuit, storing instructions for execution by the processing circuit for:

generating a fluoroscopy image of the anatomical region from the fluoroscopy system, the anatomical region including a catheter;

generating a 3D model of the anatomical region from a second image acquisition system of a different modality;

analyzing the fluoroscopy image and the 3D model with respect to a common anatomical reference system;

registering the 3D model with the fluoroscopy image in response to the common reference system and discernible parameters associated with the catheter in both the fluoroscopy system and the second image acquisition system; and registering the 3D model with the fluoroscopy image in synchronization with cyclical movement of the anatomical region;

wherein the registering comprises generating a translation factor for translating the 3D model with respect to the fluoroscopy image, generating a rotational factor, and generating a scaling factor for adjusting the scale of the 3D model with respect to the fluoroscopy image, the scaling factor being dependent on a discernable feature of the catheter.

24. An imaging system for use in a medical intervention procedure, comprising a first image acquisition system of a first modality employing a defibrillation and/or pacing lead at an anatomical region of a patient and configured to produce a first image of the anatomical region using fluoroscopy, the first image comprising a set of fluoroscopy projection images;

a second image acquisition system of a second different modality configured to generate a 3D model of the anatomical region;

an anatomical reference system common to both the first and second image acquisition systems; and a processing circuit configured to process executable instructions for registering the 3D model with the fluoroscopy image in response to the common reference system and discernible parameters associated with the defibrillation and/or pacing lead in both the first and second image acquisition systems.

25. The imaging system of claim 24, wherein the processing circuit is further configured to process executable instructions for registering the 3D model with the fluoroscopy image in synchronization with cyclical movement of the anatomical region using a defibrillation and/or pacing lead placed in the heart.

26. The imaging system of claim 25, wherein the defibrillation and/or pacing lead has a known actual diameter, and wherein the processing circuit is further configured to process executable instructions for:

determining the apparent diameter of the defibrillation and/or pacing lead in the fluoroscopy image, comparing the apparent diameter of the defibrillation and/or pacing lead with the known actual diameter of the defibrillation and/or pacing lead, determining in response thereto an actual dimension of an anatomical structure in the anatomical region in the fluoroscopy image, matching the anatomical structure in the fluoroscopy image with the same anatomical structure in the 3D model, comparing the actual and apparent sizes of the same anatomical structure in the 3D model, and generating there from a scaling factor between the first and second image acquisition systems.

27. The imaging system of claim 24, wherein:

the defibrillation and/or pacing lead is disposed at a known anatomical structure in the anatomical region at a location defined by the intersection of a horizontal plane and the line joining the focal point of the fluoroscopy system to the projection of the defibrillation and/or pacing lead, the horizontal plane being defined by an elevation h above the anatomical reference system to the known anatomical structure in the fluoroscopy system, thereby establishing a known location of the defibrillation and/or pacing lead in the first and second image acquisition systems; and the processing circuit is further configured to process executable instructions for:

determining the actual size of the some anatomical structure in the 3D model in response to the known location of the defibrillation and/or pacing lead in the 3D model and the elevation h, comparing the actual and apparent sizes of the anatomical structure in the 3D model, and generating there from a scaling factor between the first and second image acquisition systems.

28. The imaging system of claim 24, wherein:

the first image acquisition system is further configured to produce a second set of fluoroscopy projection images, the first and second sets of projection images being generated by at least two different x-ray projections separated by an angle sufficient to produce discernibly different projection images of the anatomical region, the defibrillation and/or pacing lead being disposed at a known anatomical structure in the anatomical region; and the processing circuit is further configured to process executable instructions for:

determining the location of the defibrillation and/or pacing lead in the 3D model with respect to the focal point of the fluoroscopy system to define a dimension b by analyzing the two sets of projection images using a triangulation approach; and determining the actual size of the same anatomical structure in the 3D model in response to the known location of the defibrillation and/or pacing lead in the 3D model and the dimension b, comparing the actual and apparent sizes of the anatomical structure in the 3D model, and generating there from a scaling factor between the first and second image acquisition systems.

29. A computer program product for registering a 3D model of an anatomical region of a patient with projection images of the same from an interventional fluoroscopy system, the product comprising:

a storage medium, readable by a processing circuit, storing instructions for execution by the processing circuit for:

generating a fluoroscopy image of the anatomical region from the fluoroscopy system, the anatomical region including a defibrillation and/or pacing lead;

generating a 3D model of the anatomical region from a second image acquisition system of a different modality;

analyzing the fluoroscopy image and the 3D model with respect to a common anatomical reference system;

registering the 3D model with the fluoroscopy image in response to the common reference system and discernible parameters associated with the defibrillation and/or pacing lead in both the fluoroscopy system and the second image acquisition system; and registering the 3D model with the fluoroscopy image in synchronization with cyclical movement of the anatomical region;

wherein the registering comprises generating a translation factor for translating the 3D model with respect to the fluoroscopy image, generating a rotational factor, and generating a scaling factor for adjusting the scale of the 3D model with respect to the fluoroscopy image, the scaling factor being dependent on a discernable feature of the defibrillation and/or pacing lead.

* * * * *